(12) United States Patent
Zhou et al.

(10) Patent No.: US 6,613,781 B2
(45) Date of Patent: Sep. 2, 2003

(54) HETEROCYCLYLAKLYLINDOLE OR -AZAINDOLE COMPOUNDS AS 5-HYDROXYTRYPTAMINE-6 LIGANDS

(75) Inventors: Ping Zhou, Plainsboro, NJ (US); Michael Gerard Kelly, Thousand Oaks, CA (US); Yanfang Li, Lawrenceville, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/028,487

(22) Filed: Dec. 20, 2001

(65) Prior Publication Data

US 2002/0128477 A1 Sep. 12, 2002

Related U.S. Application Data

(60) Provisional application No. 60/257,684, filed on Dec. 22, 2000.

(51) Int. Cl.$^7$ .................... A61K 31/454; C07D 40/06
(52) U.S. Cl. .................. 514/323; 546/201; 546/277.7; 546/152; 540/602; 514/339; 514/314; 514/212
(58) Field of Search .................. 514/323, 339, 514/314, 212; 546/201, 277.7, 152; 540/602

(56) References Cited

U.S. PATENT DOCUMENTS

| | | | |
|---|---|---|---|
| 4,208,417 A | 6/1980 | Uzan | |
| 5,348,968 A | 9/1994 | Lavielle et al. | |
| 5,834,493 A | 11/1998 | Gil Quintero et al. | |
| 6,066,637 A | 5/2000 | Kelly et al. | |
| 6,100,291 A | * 8/2000 | Slassi et al. | 514/414 |
| 6,133,287 A | 10/2000 | Slassi et al. | |
| 6,191,141 B1 | 2/2001 | Edwards et al. | |

FOREIGN PATENT DOCUMENTS

| | | |
|---|---|---|
| WO | WO 99/47516 A1 | 9/1999 |
| WO | WO 99/55697 A | 11/1999 |
| WO | WO 99/65906 A1 | 12/1999 |
| WO | WO 02/32863 A1 | 4/2002 |

OTHER PUBLICATIONS

Tsai, Y. et al., N1–(Benzenesulfonyl)tryptamines as novel 5–HT6 antagonists, Biorganic & Medicinal Chemistry Letters, Oct. 6, 2000, 2295–2299, 10:20, Oxford, GB.

Taylor, E. et al., Molecular determinants for recongnition of RU 24969 analogs at central 5–hydroxytryptamine recognition sites: Use of a bilinear function and substituent volumes to describe steric fit, Molecular Pharmacology, Jul. 1, 1988, 42–53, 34:1, Baltimore, MD, USA.

Hoyer, D. and Martin, G., 5–HT receptor classification and nomenclature: towards a harmonization with the human genome, Neuropharmacology, Apr. 1, 1997, 419–428, 36, Pergamon Press, Oxford, GB.

Saudou, F., et al., 5–HT receptor subtypes: Molecular and functional diversity, Medicinal Chemistry Research, 1994, 16–84, 4:1, Birkhaeuser, Boston, MA, USA.

Hansch, C. et al., The structure–activity relationship of inhibitors of serotonin uptake and receptor binding, Journal of Computer–Aided Molecular Design, Oct. 1, 1991, 441–453, 5.5, Escom Science Publishers BV, Leiden, The Netherlands.

* cited by examiner

*Primary Examiner*—Charanjit S. Aulakh
(74) *Attorney, Agent, or Firm*—Barbara L. Lences

(57) ABSTRACT

The present invention provides a compound of formula I and the use thereof in the therapeutic treatment of disorders related to or affected by the 5-HT6 receptor

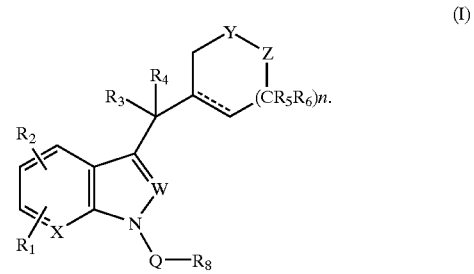

20 Claims, No Drawings

HETEROCYCLYLAKLYLINDOLE OR -AZAINDOLE COMPOUNDS AS 5-HYDROXYTRYPTAMINE-6 LIGANDS

This application claims priority from application Ser. No. 60/257,684, filed on Dec. 22, 2000, the entire disclosure of which is incorporated by reference.

BACKGROUND OF THE INVENTION

A number of central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include various 5-HT1, 5-HT2, 5-HT3, 5-HT4, 5-HT5, 5-HT6 and 5-HT7 subtypes.

The recently identified human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Northern blot analyses have revealed that 5-HT6 receptor mRNA appears to be exclusively present in the brain, with little evidence for its presence in peripheral tissues.

The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Compounds which interact with, stimulate or inhibit the 5-HT6 receptor are commonly referred to as 5-HT6 ligands. These 5-HT6 receptor ligands are believed to be of potential use in the treatment of a variety of central nervous system disorders such as anxiety, depression, epilepsy, obsessive-compulsive disorders, migraine, cognitive disorders, sleep disorders, feeding disorders, attention deficit disorders, panic attacks, disorders relating to withdrawal from drug abuse, schizophrenia, or the like or in the treatment of certain gastrointestinal disorders such as irritable bowel syndrome.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a compound of formula I

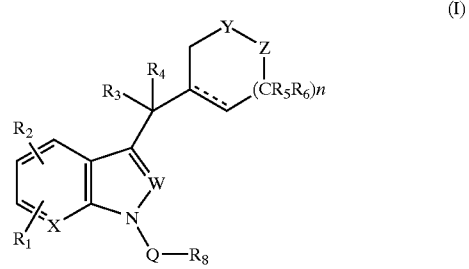

(I)

wherein
Q is $SO_2$, CO, $CONR_{24}$, $CSNR_{25}$ or $CH_2$;
W is N or $CR_7$;
X is N or $CR_9$;
Y is NR or $CR_{10}R_{29}$;
Z is $NR_{21}$ or $CR_{11}R_{30}$ with the proviso that when Y is NR then Z must be $CR_{11}R_{30}$ and with the further proviso that at least one of Y and Z must be NR or $NR_{21}$;
n is 0 or an integer of 1 or 2;
R and $R_{21}$ are each independently H, $CNR_{26}NR_{27}R_{28}$, or a $C_1$–$C_6$alkyl, $C_3$–$C_6$cycloalkyl, cycloheteroalkyl, aryl or heteroaryl group each optionally substituted;
$R_1$, $R_2$ and $R_9$ are each independently H, halogen, CN, $OCO_2R_{12}$, $CO_2R_{13}$, $CONR_{22}R_{23}$, $CNR_{14}NR_{15}R_{16}$, $SO_mR_{17}$, $NR_{18}R_{19}$, $OR_{20}$, or a $C_1$–$C_6$alkyl, $C_2$–$C_6$alkenyl, $C_2$–$C_6$alkynyl, $C_3$–$C_6$-cycloalkyl, cycloheteroalkyl, $C_1$–$C_6$alkanoyl, aryl or heteroaryl group each optionally substituted;
m is 0 or an integer of 1 or 2;
$R_3$ and $R_4$ are each independently H, halogen, $C_1$–$C_4$alkyl or $C_1$–$C_4$haloalkyl or $R_3$ and $R_4$ may be taken together with the atom to which they are attached to form a carbonyl group;
$R_5$ and $R_6$ are each independently H or an optionally substituted $C_1$–$C_6$alkyl group;
$R_7$ is H, halogen, or a $C_1$–$C_6$alkyl, $C_1$–$C_6$alkoxy, aryl or heteroaryl group each optionally substituted;
$R_8$ is an optionally substituted $C_1$–$C_6$alkyl, aryl or heteroaryl group;
$R_{10}$, $R_{11}$, $R_{29}$ and $R_{30}$ are each independently H or an optionally substituted $C_1$–$C_6$alkyl group;
$R_{12}$, $R_{13}$ and $R_{17}$ are each independently H or an optionally substituted $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group;
$R_{14}$ $R_{15}$, $R_{16}$, $R_{18}$, $R_{19}$, $R_{26}$, $R_{27}$ and $R_{28}$ are each independently H or $C_1$–$C_4$alkyl;
$R_{20}$, $R_{22}$ and $R_{23}$ are each independently H or an optionally substituted $C_1$–$C_6$alkyl group;
$R_{24}$ and $R_{25}$ are each independently H or an alkyl, aryl or heteroaryl group each optionally substituted; and
--- represents a single bond or a double bond; or
a pharmaceutically acceptable salt thereof.

The present invention further provides methods and compositions useful for the treatment of central nervous system disorders affected by or related to the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. At present, there are no known fully selective agonists. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders.

Surprisingly, it has now been found that heterocyclylalkylindole or-azaindole compounds of formula I demonstrate affinity for the 5-HT6 receptor along with significant receptor sub-type selectivity. Advantageously, said formula I compounds are effective therapeutic agents for the treatment of central nervous system (CNS) disorders associated with or affected by the 5-HT6 receptor. Accordingly, the present invention provides heterocyclylalkylindole or -azaindole compounds of formula I

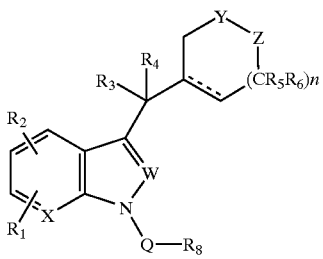

(I)

wherein
Q is $SO_2$, CO, $CONR_{24}$, $CSNR_{25}$ or $CH_2$;
W is N or $CR_7$;
X is N or $CR_9$;
Y is NR or $CR_{10}R_{29}$;
Z is $NR_{21}$ or $CR_{11}R_{30}$ with the proviso that when Y is NR then Z must be $CR_{11}R_{30}$ and with the further proviso that at least one of Y and Z must be NR or $NR_{21}$;
n is 0 or an integer of 1 or 2;
R and $R_{21}$ are each independently H, $CNR_{26}NR_{27}R_{28}$, or a $C_1$–$C_6$alkyl, $C_3$–$C_6$cycloalkyl, cycloheteroalkyl, aryl or heteroaryl group each optionally substituted;
$R_1$, $R_2$ and $R_9$ are each independently H, halogen, CN, $OCO_2R_{12}CO_2R_{13}$, $CONR_{22}R_{23}$, $CNR_{14}NR_{15}R_{16}$, $SO_mR_{17}$, $NR_{18}R_{19}$, $OR_{20}$, or a $C_1$–$C_6$alkyl, $C_2$–$C_6$alkenyl, $C_2$–$C_6$alkynyl, $C_3$–$C_6$-cycloalkyl, cycloheteroalkyl, $C_1$–$C_6$alkanoyl, aryl or heteroaryl group each optionally substituted;
m is 0 or an integer of 1 or 2;
$R_3$ and $R_4$ are each independently H, halogen, $C_1$–$C_4$alkyl or $C_1$–$C_4$haloalkyl or $R_3$ and $R_4$ may be taken together with the atom to which they are attached to form a carbonyl group;
$R_5$ and $R_6$ are each independently H or an optionally substituted $C_1$–$C_6$alkyl group;
$R_7$ is H, halogen, or a $C_1$–$C_6$alkyl, $C_1$–$C_6$alkoxy, aryl or heteroaryl group each optionally substituted;
$R_8$ is an optionally substituted $C_1$–$C_6$alkyl, aryl or heteroaryl group;
$R_{10}$, $R_{11}$, $R_{29}$ and $R_{30}$ are each independently H or an optionally substituted $C_1$–$C_6$alkyl group;

$R_{12}$, $R_{13}$ and $R_{17}$ are each independently H or an optionally substituted $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group;
$R_{14}$, $R_{15}$, $R_{16}$, $R_{18}$, $R_{19}$, $R_{26}$, $R_{27}$ and $R_{28}$ are each independently H or $C_1$–$C_4$alkyl;
$R_{20}$, $R_{22}$ and $R_{23}$ are each independently H or an optionally substituted $C_1$–$C_6$alkyl group;
$R_{24}$ and $R_{25}$ are each independently H or an alkyl, aryl or heteroaryl group each optionally substituted; and
--- represents a single bond or a double bond; or
a pharmaceutically acceptable salt thereof.

As used in the specification and claims, the term halogen designates Br, Cl, I or F; the term aryl designates phenyl or naphthyl; and the term cycloheteroalkyl designates a 5- to 7-membered monocyclic ring system containing 1 or 2 heteroatoms, which may be the same or different, selected from N, O or S and optionally containing one double bond. Exemplary of the cycloheteroalkyl ring systems included in the term as designated herein are the following rings wherein Y is NR, O or S.

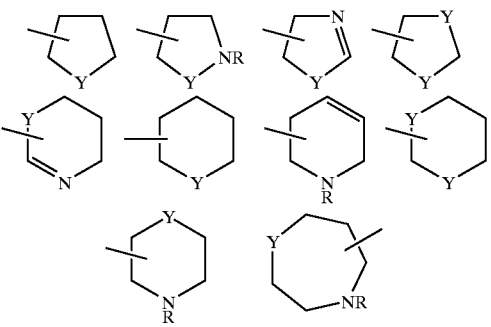

Similarly, as used in the specification and claims, the term heteroaryl designates a 5- to 10-membered monocyclic or bicyclic aromatic ring system containing 1 or 2 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl and the like. The term haloalkyl designates a $C_nH_{2n+1}$ group having from one to 2n+1 halogen atoms which may be the same or different; and the term haloalkoxy designates an $OC_nH_{2n+1}$ group having from one to 2n+1 halogen atoms which may be the same or different.

In the specification and claims, when the terms $C_1$–$C_6$alkyl, $C_2$–$C_6$alkenyl, $C_2$–$C_6$alkynl, $C_3$–$C_7$-cycloalkyl, cycloheteroalkyl, $C_1$–$C_6$-alkanoyl, aryl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl groups. Typically, up to 3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, mandelic, malonic, succinic, fumaric, acetic, lactic, nitric, sulfonic, p-toluene sulfonic, methane sulfonic acid or the like.

Preferred compounds of the invention are those compounds of formula I wherein n is 1. Also preferred are those compounds of formula I wherein $R_3$ and $R_4$ are H. Further preferred compounds of the invention are those compounds of formula I wherein Q is $SO_2$ or CO. Another preferred group of formula I compounds are those compounds wherein --- represents a single bond.

More preferred compounds of the invention are those compounds of formula I wherein Q is $SO_2$; X is $CR_9$; Y is $CR_{10}R_{29}$; Z is $NR_{21}$; and $R_3$ and $R_4$ are H. Another group of more preferred inventive compounds are those formula I compounds wherein Q is $SO_2$; X is $CR_9$; Y is $CR_{10}R_{29}$; Z is NH; $R_3$ and $R_4$ are H; $R_8$ is an optionally substituted aryl group; and --- represents a single bond.

Among the preferred compounds of the invention are:
5-fluoro-1-(phenylsulfonyl)-3-(piperidin-4-ylmethyl)-1H-indole;
5-fluoro-1-(phenylsulfonyl)-3-(1,2,5,6-tetrahydro-3-pyridinylmethyl)-1H-indole;
4-{[5-fluoro-3-(4-piperidinylmethyl)-1H-indol-1-yl]sulfonyl}aniline;
1-[(2,6-dichlorophenyl)sulfonyl]-5-fluoro-3-(4-piperidinylmethyl)-1H-indole;
1-[(3,4-dichloro-2-thienyl)sulfonyl]-5-fluoro-3-(4-piperidinylmethyl)-1H-indole;
5-fluoro-1-(1-naphthylsulfonyl)-3-(4-piperidinylmethyl)-1H-indole;
1-[(3,4-dimethoxyphenyl)sulfonyl]-5-fluoro-3-(piperidin-4-ylmethyl)-1H-indole;
4-{[5-fluoro-3-(piperidin-4-ylmethyl)-1H-indol-1-yl]sulfonyl}benzonitrile;
8-{[5-fluoro-3-(piperidin-4-ylmethyl)-1H-indol-1-yl]sulfonyl}quinoline;
1-(phenylsulfonyl)-3-(piperidin-4-ylmethyl)-1H-indole;
1-(1-naphthylsulfonyl)-3-(piperidin-4-ylmethyl)-1H-indole;
4-{[3-(piperidin-4-ylmethyl)-1H-indol-1-yl]sulfonyl}phenylamine;
1-[(3,4-dichlorothien-2-yl)sulfonyl]-3-(piperidin-4-ylmethyl)-1H-indole;
1-(phenylsulfonyl)-3-(piperidin-4-ylmethyl)-1H-pyrrolo[2,3-b]pyridine;
1-(1-naphthylsulfonyl)-3-(piperidin-4-ylmethyl)-1H-pyrrolo[2,3-b]pyridine;
4-{[3-(piperidin-4-ylmethyl)-1H-pyrrolo[2,3-b]pyridin-1-yl]sulfonyl}phenylamine;
1-[(3,4-dichlorothien-2-yl)sulfonyl]-3-(piperidin-4-ylmethyl)-1H-pyrrolo[2,3-b]pyridine;
6-flouro-1-(phenylsulfonyl)-3-(4-piperidinylmethyl)-1H-indole;
6-flouro-1-(1-naphthylsulfonyl)-3-(4-piperidinylmethyl)-1H-indole;
6-flouro-1-(3,4-dimethoxyphenylsulfonyl)-3-(4-piperidinylmethyl)-1H-indole;
6-flouro-1-(2-chlorophenylsulfonyl)-3-(4-piperidinylmethyl)-1H-indole;
6-flouro-1-(5-chlorothien-2-ylsulfonyl)-3-(4-piperidinylmethyl)-1H-indole;
6-flouro-1-(2-fluorophenylsulfonyl)-3-(4-piperidinylmethyl)-1H-indole;
6-flouro-1-(3-fluorophenylsulfonyl)-3-(4-piperidinylmethyl)-1H-indole; and
the pharmaceutically acceptable salts thereof.

Compounds of the invention may be prepared using conventional synthetic methods and, if required, standard separation or isolation techniques. For example, compounds of formula I wherein Q is $SO_2$; W is $CR_7$; Y is $CH_2$; Z is NH; n is 1; --- represents a single bond; and $R_3$ and $R_4$ are H (Ia) may be prepared by reacting a compound of formula II with 4-pyridinecarboxaldehyde to give the corresponding hydroxymethylpyridine of formula III. Said formula III compound may be fully reduced to give the piperidinylmethyl compound of formula IV. Said formula IV compound may be protected with a group such as t-butyl carbonate (Boc) to give the protected compound of formula V and the protected compound may then be sulfonated using the appropriate sulfonyl halide reagent and deprotected to give the desired formula Ia compound. The reaction sequence is shown in flow diagram I.

FLOW DIAGRAM I

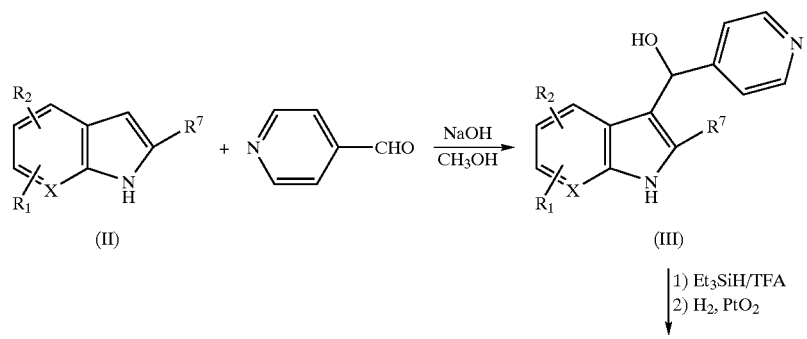

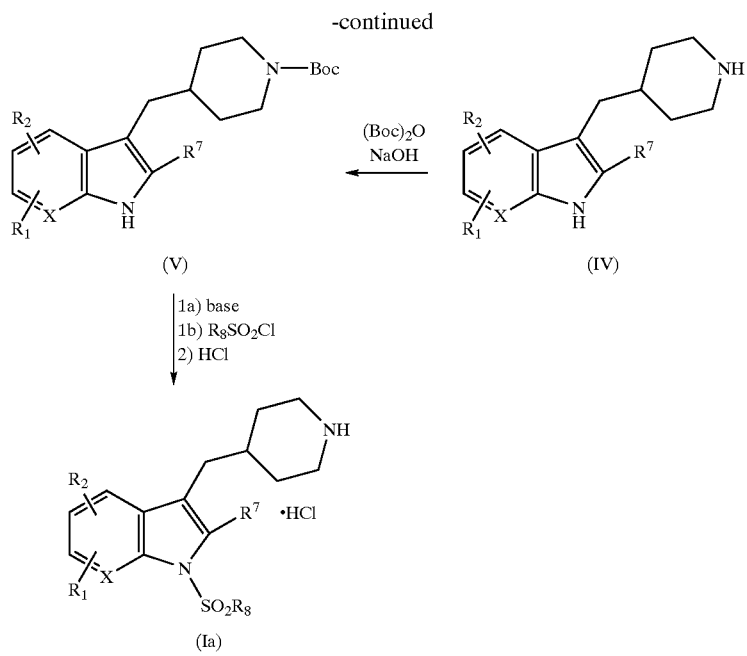

Compounds of formula I wherein --- represents a double bond; Q is $SO_2$; Y is NH; Z is $CH_2$; n is 1; and $R_3$ and $R_4$ are H(Ib) may be prepared by reacting the formula II substrate with 3-pyridine carboxaldehyde to form the corresponding hydroxymethylpyridine compound of formula VI; partially reducing said formula VI compound to give the indolyl- or azaindolylmethylpyridine of formula VII; reacting said formula VII pyridine with benzylbromide to form the pyridinium bromide of formula VIII, reacting the formula VIII pyridinium salt with $NaBH_4$ to give the tetrahydro-3-pyridinylmethyl compound of formula IX; debenzylating said formula IX compound with chloroethyl-chloroformate to give the compound of formula X; and then sequentially protecting, sulfonating and deprotecting said formula X compound as described hereinabove to give the desired formula Ib compound. The reaction sequence is shown in flow diagram II, wherein G represents a protecting group and φ represents a phenyl group.

Flow Diagram II

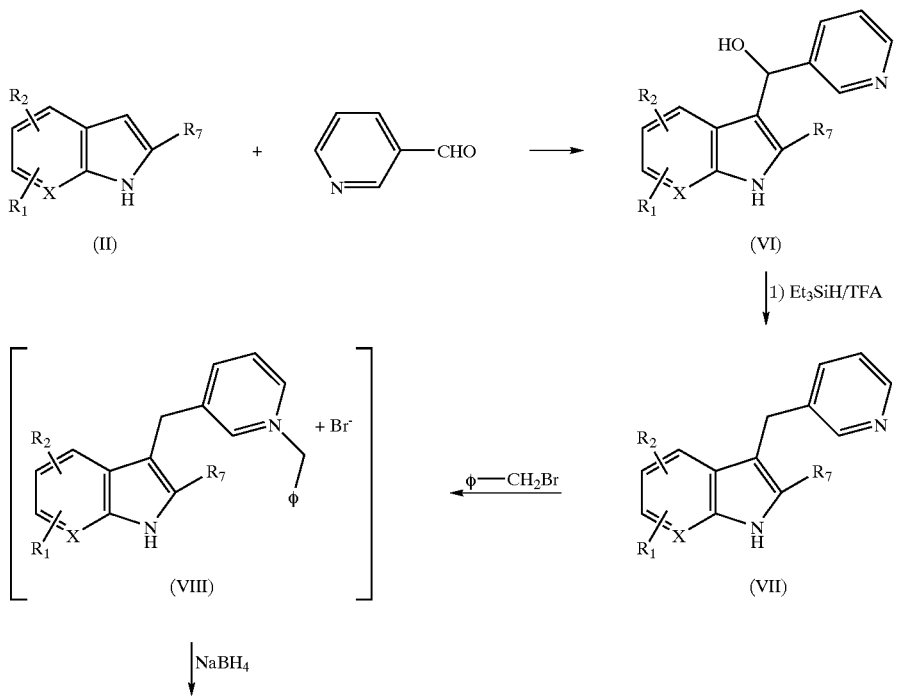

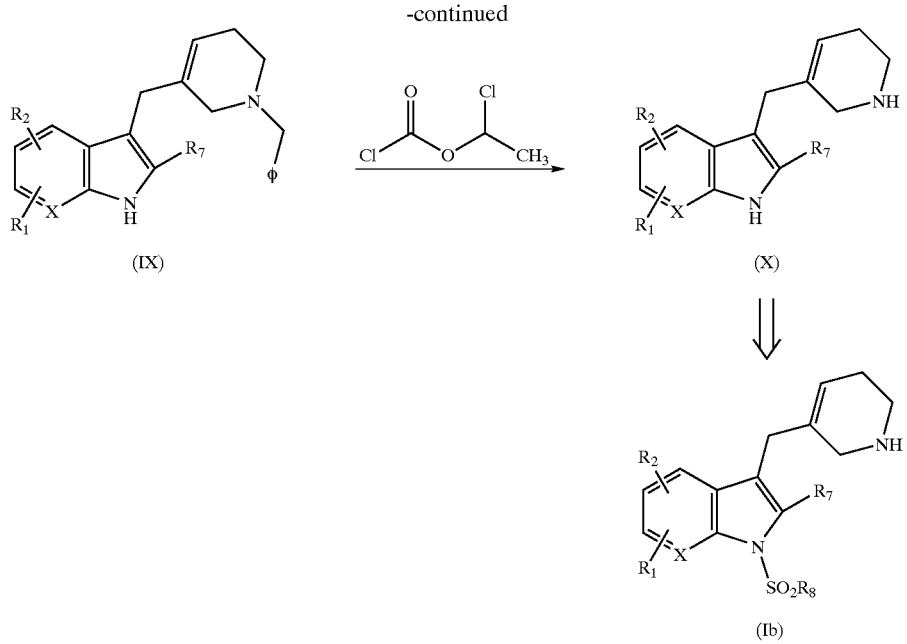

Compounds of formula I wherein R and $R_{21}$ are other than hydrogen may be prepared by alkylating a compound of formula Ia or Ib with an appropriate alkylating agent such as an alkyl halide. Compounds of formula I wherein Q is CO, $CONR_{24}$ or $CH_2$ may be prepared by reacting a protected compound of formula V or formula IX with a carbonyl halide, carbamoyl halide or alkyl halide respectively. Employing these and other literature procedures, the formula I compounds of the invention may be prepared.

Advantageously, the inventive compound of formula I may be utilized in the treatment of central nervous system disorders relating to or affected by the 5-HT6 receptor such as motor, mood, psychiatric, cognitive, neurodegenerative, or the like disorders. In particular, CNS disorders such as anxiety, depression, schizophrenia, Alzheimer's disease, Parkinson's disease, eating disorders, disorders related to alcohol or drug withdrawal, sexual dysfunction, attention deficit disorder, memory loss or the like. Accordingly, the present invention provides a method for the treatment of a disorder of the central nervous system (CNS) related to or affected by the 5-HT6 receptor in a patient in need thereof which comprises providing said patient with a therapeutically effective amount of a compound of formula I as described hereinabove. The compounds may be provided via oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are administered in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmoregulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms HPLC and NMR designate high performance liquid chromatography and nuclear magnetic resonance, respectively.

EXAMPLE 1

Preparation of (5-Fluoro-1H-indol-3-yl)(4-pyridinyl)-methanol

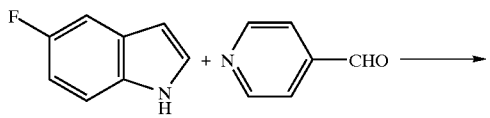

A stirred solution of 5-fluoroindole (3.10 g, 23.0 mmol) in methanol is treated with 4-pyridinecarbox-aldehyde (2.20 ml, 23.0 mmol), then treated with aqueous NaOH (2.5 ml, 50%) at 0° C., stirred for 1 hr at 0° C., warmed to room temperature, stirred for 3 hr. and diluted with water. The resultant mixture is filtered. The filtercake is dried under vacuum to afford the title product as a light yellow solid, 5.2 g (93%) mp 171–173° C., identified by mass spectral and NMR analyses.

EXAMPLE 2

Preparation of 5-Fluoro-3-(4-pyridinylmethyl)-1H-indole

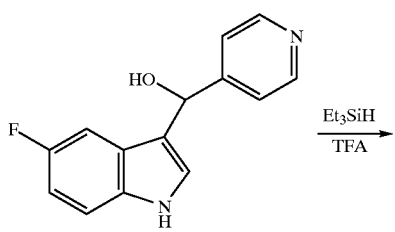

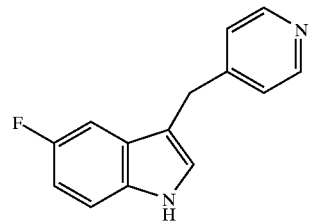

A suspension of (5-fluoro-1H-indol-3-yl)-pyridin-4-yl-methanol (3.36 g, 13.9 mmol) in methylene chloride is treated with triethylsilane (2.48 ml, 15.5 mmol) followed by trifluoroacetic acid (11.9 ml, 155 mmol) at room temperature, stirred overnight and concentrated in vacuo. The resultant residue is treated with saturated $Na_2CO_3$ to pH>9 and extracted with methylene chloride. The combined extracts are washed sequentially with water and brine, dried over $Na_2SO_4$ and concentrated in vacuo. This residue is purified by flash chromatography (silica gel, $CH_2Cl_2$/MeOH: 95/5) to give the title product as a white solid, 2.5 g (80%) mp 141–142° C. (lit. mp 149° C., Malleron et al, J. Med. Chem. 1993, 36, 1194).

EXAMPLE 3

Preparation of 5-Fluoro-3-(4-piperidinylmethyl)-1H-indole

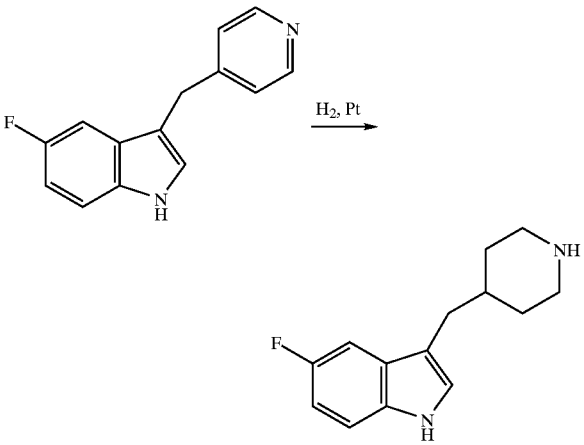

A mixture of 5-fluoro-3-(4-pyridinylmethyl)-1H-indole (4.50 g, 20 mmol) and $PtO_2$ (0.50 g, 2.2 mmol) in ethanol and acetic acid is hydrogenated under 45 psi at room temperature for 48 hr. After filtration of the catalyst and concentration of the filtrate, the residue is taken up with water, basified to pH 11 with 1N NaOH and extracted with $CH_2Cl_2$/iPrOH (3/1). The combined extracts are dried over $Na_2SO_4$ and concentrated in vacuo to give a pink solid. The solid is crystallized from EtOAc to afford the title compound as a white solid, 4.0 g (86%) mp 155–157° C. (Lit. mp 163° C., Malleron et al, J. Med. Chem. 1193,36,1194).

EXAMPLE 4

Preparation of tert-Butyl 4-[(5-fluoro-1H-indol-3-yl)methyl]-1-piperidinecarboxylate

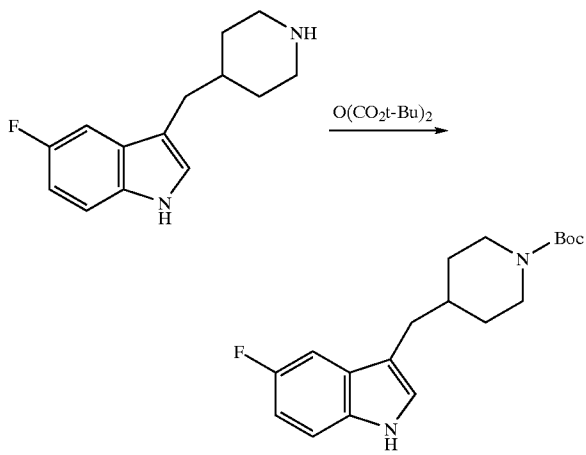

A solution of 5-fluoro-3-(4-piperidinylmethyl)-1H-indole (1.0 g, 4.3 mmol) and di-tert-butyl dicarbonate (0.94 g, 4.3 mmol) in 1N NaOH and dioxane is stirred under nitrogen at room temperature for 24 hr, quenched with water and diluted with ethyl acetate. The organic phase is separated, washed with H$_2$O and saturated NaCl, dried over MgSO$_4$, and concentrated in vacuo. The resultant residue is purified by flash chromatography (silica gel, EtOAc/hexane: 2/8) to afford the title compound as a white solid, 1.4 g, mp 144–145° C., identified by NMR and mass spectral analyses.

EXAMPLE 5

Preparation of tert-Butyl 4-{[5-fluoro-1-(phenylsulfonyl)-1H-indol-3-yl)methyl]-1-piperidinecarboxylate

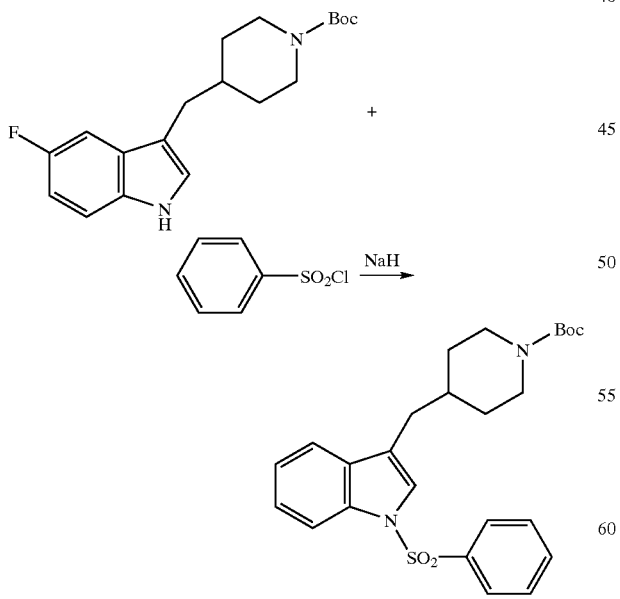

A stirred solution of tert-butyl 4-[(5-fluoro-1H-indol-3-yl)methyl]-1-piperidinecarboxylate (665 mg, 2.0 mmol) in tetrahydrofuran is treated with NaH (60% in mineral oil, 120 mg, 3.0 mmol) portion-wise, under nitrogen, at room temperature, stirred for 0.5 hr, treated with benzenesulfonyl chloride (0.38 ml, 3.0 mmol), stirred for 18 hr under nitrogen at room temperature, quenched with water and diluted with ethyl acetate. The resultant phases are separated and the organic phase is washed with water and saturated NaCl, dried over MgSO$_4$ and concentrated in vacuo. The resultant residue is purified by flash chromatography (silica gel, EtOAc/hexane, 2/8) to afford the title compound as a white solid, 740 mg, mp 155–157° C., identified by NMR and mass spectral analyses.

EXAMPLE 6

Preparation of 5-Fluoro-1-phenylsulfonyl)-3-(4-piperidinylmethyl)-1H-indole hydrochloride

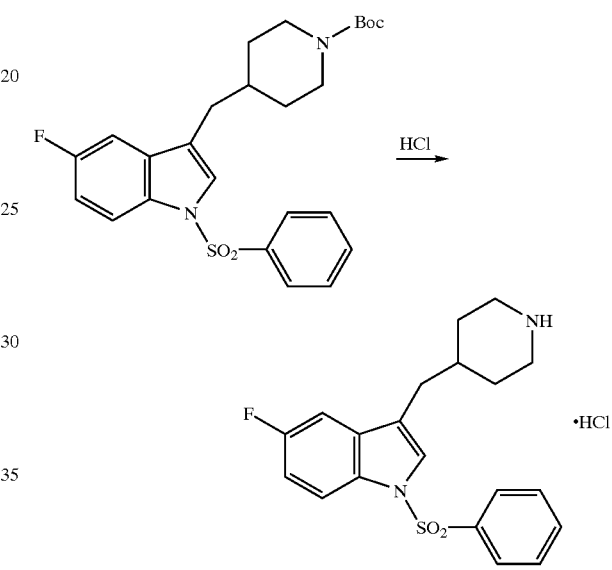

A solution of tert-butyl 4-{[5-fluoro-1-(phenylsulfonyl)-1H-indol-3-yl)methyl]-1-piperidine carboxylate (637 mg, 1.35 mmol) in methanol and HCl (1M in Et$_2$O, 7.0 ml) is heated at reflux temperature under N$_2$ for 18 hr and concentrated in vacuo. The resultant residue is diluted with ether and filtered. The filtercake is dried under vacuum to give the title product as an off-white solid, 500 mg, mp 233–235° C., (dec.), identified by NMR and mass spectral analyses.

EXAMPLE 7

Preparation of 4-{[5-Fluoro-3-(4-piperidinylmethyl)-1H-indol-1-yl]sulfonyl}aniline

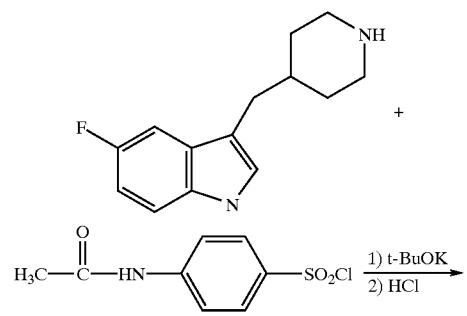
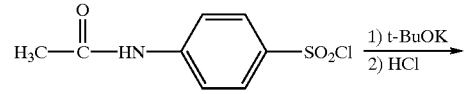

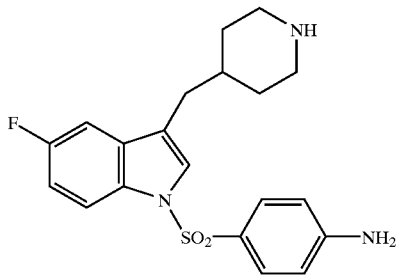

A stirred solution of tert-butyl 4-[(5-fluoro-1H-indol-3-yl)methyl]-1-piperidinecarboxylate (332 mg, 1.0 mmol) in tetrahydofuran (THF) is treated with tBuOK (1.1 ml, 1.1 mmol, 1M in THF solution) under nitrogen at room temperature, stirred for 0.5 hr, treated with N-acetylsulfonilyl chloride (234 mg, 1.0 mmol), stirred for 18 hr and concentrated in vacuo. The resultant residue is treated with methanol, followed by 1N HCl (2 ml) heated at reflux temperature for 3 hr, cooled and concentrated in vacuo. This residue is dissolved in isopropanol, treated with 1N NaOH to pH>9 and filtered. The filtercake is washed with water and dried under vaccum to afford the title compound as an off-white solid, 170 mg, mp 162–164° C., identified by NMR and mass spectral analyses.

EXAMPLE 8

Preparation of 1-[2,6-Dichlorophenyl)sulfonyl]-5-fluoro-3-(4-piperidinylmethyl)-1H-indole hydrochloride

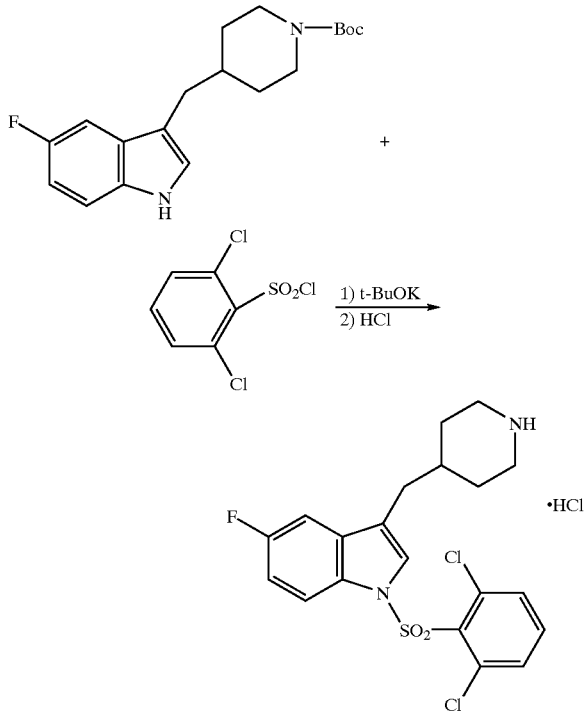

A stirred solution of tert-butyl 4-[(5-fluoro-1H-indol-3-yl)methyl]-1-piperidinecarboxylate (332 mg, 1.0 mmol) in tetrahydrofuran (THF) is treated with tBuOK (1.1 ml, 1.1 mmol, 1M in THF solution) under nitrogen at room temperature, stirred for 0.5 hr, treated with 2,6-dichlorobenzenesulfonyl chloride (246 mg, 1.0 mmol), stirred for 18 hr at room temperature, quenched with water and diluted with ethyl acetate. The phases are separated and the organic phase is dried over $Na_2SO_4$ and concentrated in vacuo. The resultant residue is treated with methanol and 1N HCl (2 ml), heated at reflux temperature for 3 hr, cooled, and filtered. The filtercake is washed with ethyl acetate and dried to afford the title compound as a white solid, 338 mg, mp 288–290° C., identified by NMR and mass spectral analyses.

EXAMPLE 9

Preparation of 1-[3,4-Dichloro-2-thienyl)sulfonyl]-5-fluoro-3-(4-piperidinylmethyl)-1H-indole hydrochloride

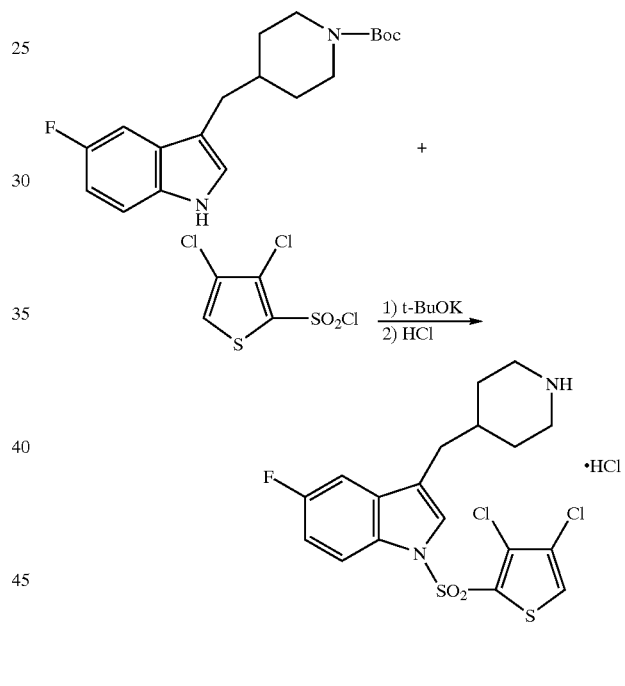

A stirred solution of tert-butyl 4-[(5-fluoro-1H-indol-3-yl)methyl]-1-piperidinecarboxylate (332 mg, 1.0 mmol) in tetrahydrofuran (THF) is treated with tBuOK (1.1 ml, 1.1 mmol, 1M in THF solution) under nitrogen at room temperature, stirred for 0.5 hr, treated with (3,4-dichlorothien-2-yl)sulfonyl chloride (252 mg, 1.0 mmol), stirred for 18 hr at room temperature, quenched with water and diluted with ethyl acetate. The phases are separated and the organic phase is dried over $Na_2SO_4$ and concentrated in vacuo. The resultant residue is treated with methanol, followed by 1N HCl (2 ml), heated at reflux temperature for 3 hr, cooled and filtered. The filtercake is washed with ethyl acetate and dried to afford the title compound as an off-white solid, 327 mg, mp 205–207° C., identified by NMR and mass spectral analyses.

EXAMPLE 10

Preparation of 5-Fluoro-1-(1-naphthylsulfonyl)-3-(4-piperidinylmethyl)-1H-indole hydrochloride

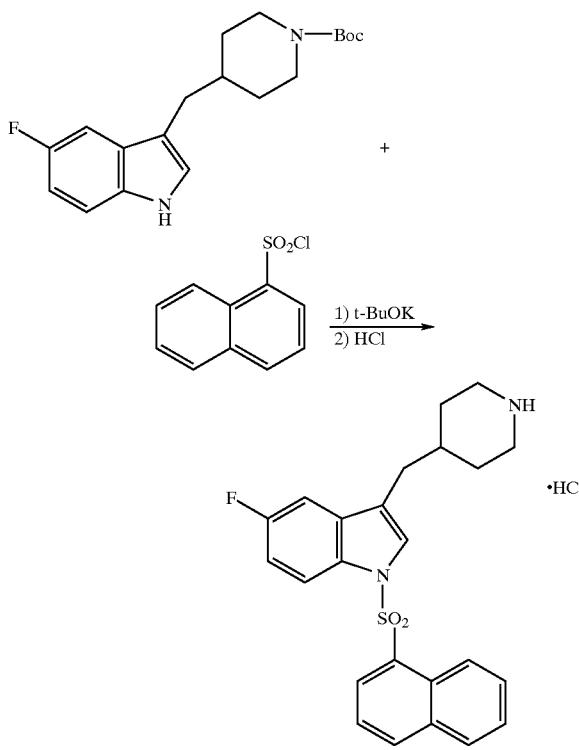

Using essentially the same procedure described in Example 9 and substituting naphthalenesulfonyl chloride, the title product is obtained as a white solid, 346 mg, mp 295–297° C., identified by NMR and mass spectral analyses.

EXAMPLE 11

Preparation of (5-Fluoro-1H-indol-3-yl)(3-pyridinyl)methanol

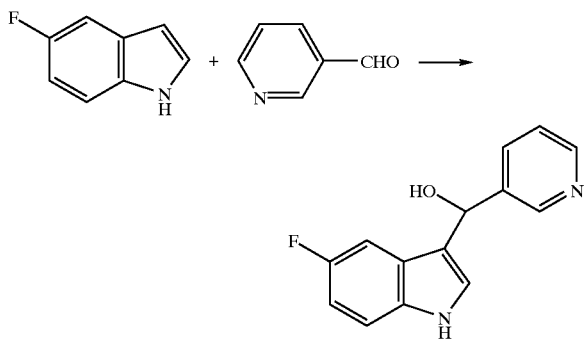

A stirred solution of 5-fluoroindole (4 g, 30 mmol) in methanol is treated with 3-pyridine carboxaldehyde (2.79 ml, 30 mmol), cooled to 0° C., treated with 50% NaOH (3.25 ml), stirred at 0° C. for 1 hr, warmed to room temperature, stirred for 3 hr, treated with water and extracted with ethyl acetate. The extracts are combined, dried over $Na_2SO_4$ and concentrated in vacuo. The residue is treated with ethyl acetate and filtered. The filtrate is further concentrated and filtered. The filtercakes are combined and dried to afford the title compound as a pale orange solid 5.2 g (73%) mp 131–133° C., identified by NMR and mass spectral analyses.

EXAMPLE 12

Preparation of 5-Fluoro-3-(3-pyridinylmethyl)-1H-indole

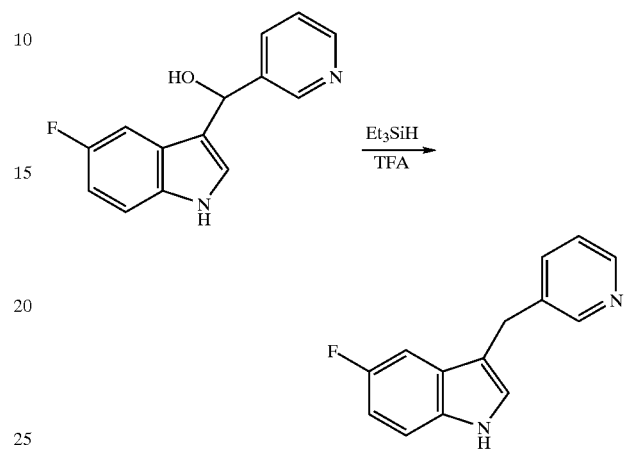

A suspension of (5-fluoro-1H-indole-3-yl)-pyridin-3-yl-methanol (5.00 g, 21 mmol) in methylene chloride is treated with triethylsilane (3.70 ml, 23 mmol) and trifluoroacetic acid (TFA), stirred at room temperature overnight, and concentrated in vacuo. The resultant residue is basified with 2.5 N NaOH and saturated $NaHCO_3$, and extracted with methylene chloride. The extracts are combined, dried over $Na_2SO_4$ and concentrated in vacuo. This residue is purified by column chromatography (50%EtOAc/$CH_2Cl_2$) to give the title compound as a pale orange solid 3.24 g (68%) mp 109–112° C., identified by NMR and mass spectral analyses.

EXAMPLE 13

Preparation of 3-[(1-Benzyl-1,2,3,6-tetrahydro-3-pyridinyl)methyl]-5-fluoro-1H-indole

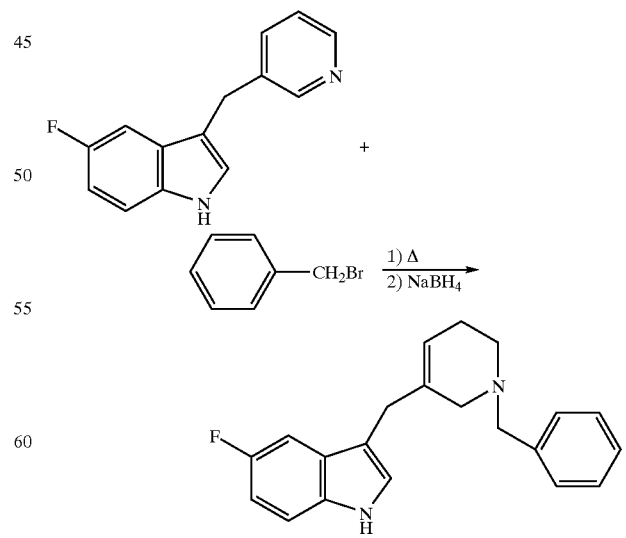

A solution of 5-fluoro-3-pyridin-3-yl-1H-indole (1.2 g, 5.3 mmol) in methyl ethyl ketone is treated with benzyl bromide (4.32 ml, 35.4 mmol), heated at reflux temperature for 3 hr, cooled and decanted. The resulting oil is stirred with ether to remove residual benzyl bromide and decanted. The remaining residue is dissolved in methanol, cooled to 0° C., treated with crushed NaBH₄ (670 mg) pellets, stirred at 0° C. for 1 hr, quenched with saturated NaHCO₃ and concentrated in vacuo. The resultant aqueous solution is extracted with methylene chloride. The extracts are combined, dried over Na₂SO₄ and concentrated in vacuo. The resulting yellow foam residue is purified by column chromatography (40% EtOAc/hexanes) to give the title compound as a pale yellow solid, 730 mg (43%) mp 133–136° C., identified by NMR and mass spectral analyses.

EXAMPLE 14

Preparation of 5-Fluoro-3-(1,2,3,6-tetrahydro-3-pyridinylmethyl)-1H-indole

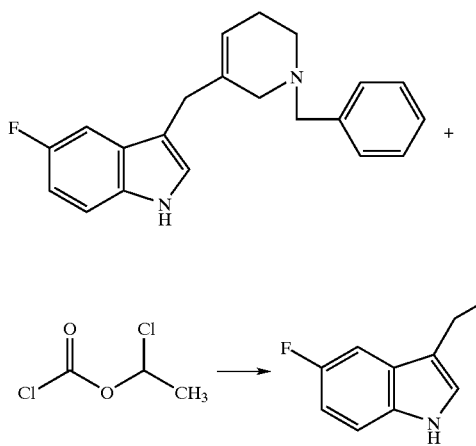

A solution of 3-[(1-benzyl-1,2,3,6-tetrahydro-3-pyridinyl)methyl]-5-fluoro-1H-indole (500 mg, 1.57 mmol) in dichloroethane is treated with chloroethylchloro-formate (0.51 mL, 4.7 mmol), stirred at 80° C. for 4.5 hr, cooled and concentrated in vacuo to give a residue. The residue is treated with methanol, heated at reflux temperature overnight, cooled and concentrated in vacuo. The resultant residue is purified by column chromatography (10% MeOH/CH₂Cl₂+NH₄OH) to give the title compound as a pale yellow solid, 240 mg (66%) mp 145° C. (dec.), identified by NMR and mass spectral analyses.

EXAMPLE 15

Preparation of tert-Butyl 5-[(5-fluoro-1H-indol-3-yl)methyl]-3,6-dihydro-1(2H)-pyridinecarboxylate

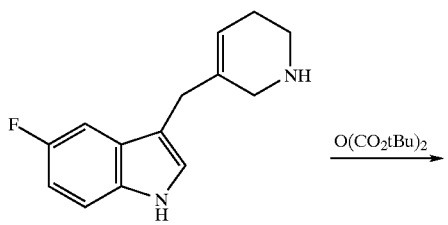

-continued

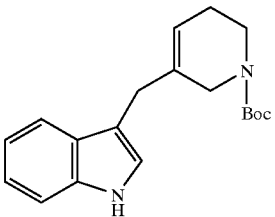

A mixture of 5-fluoro-3-(1,2,3,6-tetrahydro-3-pyridinylmethyl)-1H-indole (0.53 g, 2.3 mmol) and di-tert-butyl dicarbonate (0.55 g, 2.5 mmol) in 1N NaOH(2.5 ml) and dioxane is stirred under nitrogen at room temperature for 18 hr, quenched with water and diluted with ethyl acetate. The organic phase is separated, washed with water and saturated NaCl, dried over MgSO₄ and concentrated in vacuo. The resultant residue is purified by flash chromatography (silica gel, EtOAc/hexane: 3/7) to afford the title compound as a yellow foam, 0.46 g, mp 78–80° C., identified by NMR and mass spectral analyses.

EXAMPLE 16

Preparation of tert-Butyl 5-{[5-fluoro-1-(phenyl-sulfonyl)-1H-indol-3-yl]methyl}-3,6-dihydro-1(2H)-pyridinecarboxylate

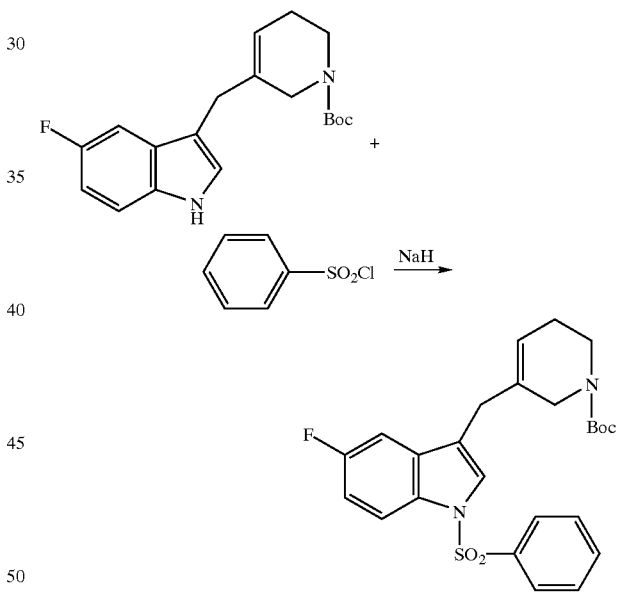

A stirred solution of tert-butyl 5-[(5-fluoro-1H-indol-3-yl)methyl]-3,6-dihydro-1(2H)-pyridinecarboxylate (430 mg, 1.30 mmol) in tetrahydrofuran is treated with NaH (60% in mineral oil, 78 mg, 1.95 mmol) portion-wise under nitrogen at room temperature, stirred for 0.5 hr, treated with benzenesulfonyl chloride (0.25 ml, 1.95 mmol), stirred for 17 hr under nitrogen at room temperature, quenched with ice-water and diluted with ethyl acetate. The phases are separated and the aqueous phase is extracted with ethyl acetate. The combined extracts and organic phase are washed with water and saturated NaCl, dried over MgSO₄ and concentrated in vacuo. The resultant residue is purified by flash chromatography (silica gel, EtOAc/hexane, 1/9) to afford the title compound as a yellow solid, 350 mg, mp 63–65° C., identified by NMR and mass spectral analyses.

EXAMPLE 17

Preparation of 5-Fluoro-1-(phenylsulfonyl)-3-(1,2,5,6-tetrahydro-3-pyridinylmethyl)-1H-indole hydrochloride

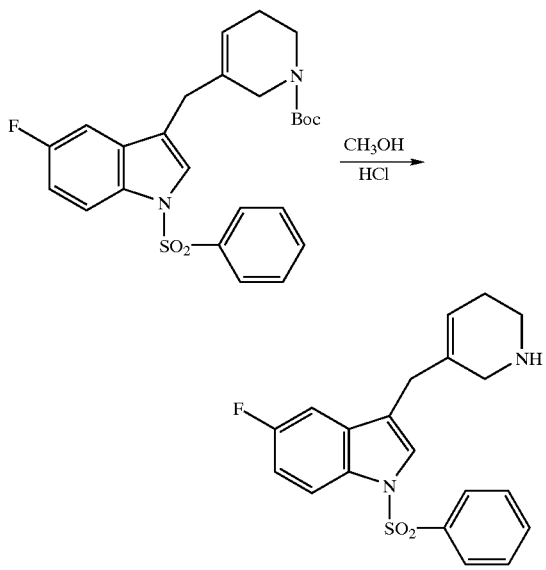

A solution of tert-butyl 5-{[5-fluoro-1-(phenylsulfonyl)-1H-indol-3-yl]methyl}-3,6-dihydro-1(2H)-pyridinecarboxylate (320 mg, 0.68 mmol) in methanol and HCl (1M in $Et_2O$, 1.0 ml) is heated at reflux temperature under nitrogen for 18 hr, cooled and concentrated in vacuo. The resultant residue is treated with ether and filtered. The filtercake is dried in vacuo to afford the title compound as a brown solid, 211 mg, mp 96° C. (dec.), identified by NMR and mass spectral analyses.

EXAMPLES 18–28

Preparation of 1-Arylsulfonyl-substituted-3[(4-piperidinyl)methyl]indole hydrochloride

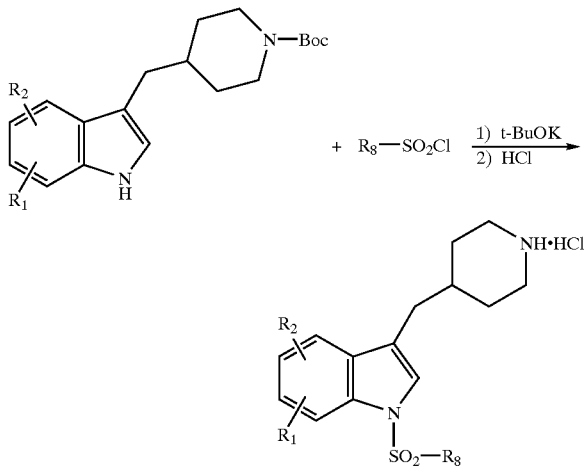

Using essentially the same procedures described hereinabove and employing the appropriate indole substrate and arylsulfonyl chloride, the compounds shown in Table I are obtained and identified by mass spectral and NMR analyses.

TABLE I

| Ex. No. | $R_1$ | $R_2$ | $R_8$ | mp ° C. |
|---|---|---|---|---|
| 18 | H | 5-F | 3,4-dimethoxyphenyl | 246 dec |
| 19 | H | 5-F | 4-benzonitrile | 249 dec |
| 20 | H | 5-F | quinolin-8-yl | 245 dec |
| 21 | 6-F | H | phenyl | >250 dec |
| 22 | 6-F | H | 1-naphthyl | 265 dec |
| 23 | 6-F | H | 3,4-dimethoxyphenyl | 218–220 dec |
| 24 | 6-F | H | 2-chlorophenyl | 249–251 dec |
| 25 | 6-F | H | 5-chlorothien-2-yl | 227–229 dec |
| 26 | 6-F | H | 2-fluorophenyl | 206–208 dec |
| 27 | 6-F | H | 3-fluorophenyl | 240 dec |
| 28 | 6-F | H | 4-aminophenyl | 198–200 |

EXAMPLE 21

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM $MgCl_2$ and 0.5 mM EDTA and 20 μl of [$^3$H]-LSD (S.A., 86.0 Ci/mmol, available from Amersham Life Science), 3.0 nM. The dissociation constant, $K_D$, of the [$^3$H]LSD at the human serotonin 5-HT6receptor is 2.9 nM, as determined by saturation binding with increasing concentrations of [$^3$H] LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196 Harvester. The bound complex caught on the filter disk is allowed to air dry and the radioactivity is measured in a Packard TopCount® equipped with six photomultiplier detectors, after the addition of 40.0 µl Microscint®-20 scintillant to each shallow well. The unifilter plate is heat-sealed and counted in a PackardTop-Count® with a tritium efficiency of 31.0%.

Specific binding to the 5-HT6 receptor is defined as the total radioactivity bound less the amount bound in the presence of 10.0 µM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determine and compared to those values obtained by representative compounds known to demonstrate binding to the 5-HT6 The data are shown in Table II, below.

TABLE II

| Test Compound (Ex. No.) | 5-HT6 Binding Ki (nM) |
|---|---|
| 6 | 12.0 |
| 7 | 1.0 |
| 10 | 13.0 |
| 18 | 8.0 |
| 19 | 162.0 |
| 20 | 2.0 |
| 21 | 13.0 |
| 22 | 24.0 |
| 23 | 19.0 |
| 24 | 13.0 |
| 25 | 18.0 |
| 26 | 17.0 |
| 27 | 29.0 |
| 28 | 3.0 |
| Comparative Examples | 15 |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

As can be seen from the results set forth above, the compounds of the invention demonstrate a high degree of affinity for the 5-HT6 receptor.

What is claimed is:
1. A compound of formula I

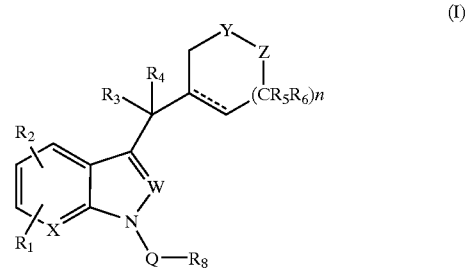

wherein
Q is $SO_2$, CO, $CONR_{24}$, $CSNR_{25}$;
W is N or $CR_7$;
X is N or $CR_9$;
Y is NR or $CR_{10}R_{29}$;
Z is $NR_{21}$ or $CR_{11}R_{30}$ with the proviso that when Y is NR then Z must be $CR_{11}R_{30}$ and with the further proviso that at least one of Y and Z must be NR or $NR_{21}$;
n is an integer of 1 or 2;
R and $R_{21}$ are each independently H, $CNR_{26}NR_{27}R_{28}$, or a $C_1$–$C_6$alkyl, $C_3$–$C_6$cycloalkyl, cycloheteroalkyl, aryl or heteroaryl group each optionally substituted;
$R_1$, $R_2$ and $R_9$ are each independently H, halogen, CN, $OCO_2R_{12}$, $CO_2R_{13}$, $CONR_{22}R_{23}$, $CNR_{14}NR_{15}R_{16}$, $SO_mR_{17}$, $NR_{18}R_{19}$, $OR_{20}$, or a $C_1$–$C_6$alkyl, $C_2$–$C_6$alkenyl, $C_2$–$C_6$alkynyl, $C_3$–$C_6$-cycloalkyl, cycloheteroalkyl, $C_1$–$C_6$alkanoyl, aryl or heteroaryl group each optionally substituted;
m is 0 or an integer of 1 or 2;
$R_3$ and $R_4$ are each independently H, halogen, $C_1$–$C_4$alkyl or $C_1$–$C_4$haloalkyl or $R_3$ and $R_4$ may be taken together with the atom to which they are attached to form a carbonyl group;
$R_5$ and $R_6$ are each independently H or an optionally substituted $C_1$–$C_6$alkyl group;
$R_7$ is H, halogen, or a $C_1$–$C_6$alkyl, $C_1$–$C_6$alkoxy, aryl or heteroaryl group each optionally substituted;
$R_8$ is an optionally substituted $C_1$–$C_6$alkyl, aryl or heteroaryl group;
$R_{10}$, $R_{11}$, $R_{29}$ and $R_{30}$ are each independently H or an optionally substituted $C_1$–$C_6$alkyl group;
$R_{12}$, $R_{13}$ and $R_{17}$ are each independently H or an optionally substituted $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group;
$R_{14}$, $R_{15}$, $R_{16}$, $R_{18}$, $R_{19}$, $R_{26}$, $R_{27}$ and $R_{28}$ are each independently H or $C_1$–$C_4$alkyl;
$R_{20}$, $R_{22}$ and $R_{23}$ are each independently H or an optionally substituted $C_1$–$C_6$alkyl group;
$R_{24}$ and $R_{25}$ are each independently H or an alkyl, aryl or heteroaryl group each optionally substituted; and
--- represents a single bond or a double bond; or a pharmaceutically acceptable salt thereof.
2. The compound according to claim 1 wherein n is 1.
3. The compound according to claim 1 wherein $R_3$ and $R_4$ are H.
4. The compound according to claim 1 wherein Q is $SO_2$ or CO.-

5. The compound according to claim 1 wherein --- represents a single bond.

6. The compound according to claim 2 wherein X is $CR_9$; Y is $CR_{10}R_{29}$; Z is $NR_{21}$; $R_3$ and $R_4$ are H; and --- represents a single bond.

7. The compound according to claim 6 wherein Q is $SO_2$; $R_{21}$ is H; $R_8$ is an optionally substituted aryl group; and --- represents a single bond.

8. The compound according to claim 4 selected from the group consisting of:

5-fluoro-1-(phenylsulfonyl)-3-(piperidin-4-ylmethyl)-1H-indole;

5-fluoro-1-(phenylsulfonyl)-3-(1,2,5,6-tetrahydro-3-pyridinylmethyl)-1H-indole;

4-{[5-fluoro-3-(4-piperidinylmethyl)-1H-indol-1yl]sulfonyl}aniline;

1-[(2,6-dichlorophenyl)sulfonyl]-5-fluoro-3-(4-piperidinylmethyl)-1H-indole;

1-[(3,4-dichloro-2-thienyl)sulfonyl]-5-fluoro-3-(4-piperidinylmethyl)-1H-indole;

5-fluoro-1-(1-naphthylsulfonyl)-3-(4-piperidinylmethyl)-1H-indole;

1-[(3,4-dimethoxyphenyl)sulfonyl]-5-fluoro-3-(piperidin-4-ylmethyl)-1H-indole;

4-{[5-fluoro-3-(piperidin-4-ylmethyl)-1H-indol-1-yl]sulfonyl}benzonitrile;

8-{[5-fluoro-3-(piperidin-4-ylmethyl)-1H-indol-1-yl]sulfonyl}quinoline;

1-(phenylsulfonyl)-3-(piperidin-4-ylmethyl)-1H-indole;

1-(1-naphthylsulfonyl)-3-(piperidin-4-ylmethyl)-1H-indole;

4-{[3-(piperidin-4-ylmethyl)-1H-indol-1-yl]sulfonyl}phenylamine;

1-[(3,4-dichlorothien-2-yl)sulfonyl]-3-(piperidin-4-ylmethyl)-1H-indole;

6-flouro-1-(phenylsulfonyl)-3-(4-piperidinylmethyl)-1H-indole;

6-flouro-1-(1-naphthylsulfonyl)-3-(4-piperidinylmethyl)-1H-indole;

6-flouro-1-(3,4-dimethoxyphenylsulfonyl)-3-(4-piperidinylmethyl)-1H-indole;

6-flouro-1-(2-chlorophenylsulfonyl)-3-(4-piperidinylmethyl)-1H-indole;

6-flouro-1-(5-chlorothien-2-ylsulfonyl)-3-(4-piperidinylmethyl)-1H-indole;

6-flouro-1-(2-fluorophenylsulfonyl)-3-(4-piperidinylmethyl)-1H-indole;

6-flouro-1-(3-fluorophenylsulfonyl)-3-(4-piperidinylmethyl)-1H-indole; and a pharmaceutically acceptable salt thereof.

9. A method for the treatment of a disorder of the central nervous system related to or affected by the 5-HT6 receptor in a patient in need thereof which comprises providing said patient with a therapeutically effective amount of a compound of formula I

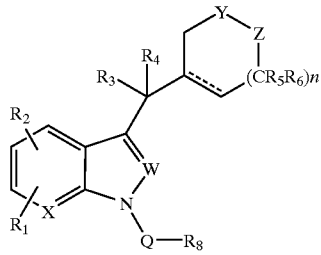

wherein
Q is $SO_2$, CO, $CONR_{24}$, or $CSNR_{25}$
W is N or $CR_7$;
X is N or $CR_9$;
Y is NR or $CR_{10}R_{29}$;
Z is $NR_{21}$ or $CR_{11}R_{30}$ with the proviso that when Y is NR then Z must be $CR_{11}R_{30}$ and with the further proviso that at least one of Y and Z must be NR or $NR_{21}$;
n is an integer of 1 or 2;
R and $R_{21}$ are each independently H, $CNR_{26}NR_{27}R_{28}$, or a $C_1$–$C_6$alkyl, $C_3$–$C_6$cycloalkyl, cycloheteroalkyl, aryl or heteroaryl group each optionally substituted;
$R_1$, $R_2$ and $R_9$ are each independently H, halogen, CN, $OCO_2R_{12}$, $CO_2R_{13}$, $CONR_{22}R_{23}$, $CNR_{14}NR_{15}R_{16}$, $SO_mR_{17}$, $NR_{18}R_{19}$, $OR_{20}$, or a $C_1$–$C_6$alkyl, $C_2$–$C_6$alkenyl, $C_2$–$C_6$alkynyl, $C_3$–$C_6$-cycloalkyl, cycloheteroalkyl, $C_1$–$C_6$alkanoyl, aryl or heteroaryl group each optionally substituted;
m is 0 or an integer of 1 or 2;
$R_3$ and $R_4$ are each independently H, halogen, $C_1$–$C_4$alkyl or $C_1$–$C_4$haloalkyl or $R_3$ and $R_4$ may be taken together with the atom to which they are attached to form a carbonyl group;
$R_5$ and $R_6$ are each independently H or an optionally substituted $C_1$–$C_6$alkyl group;
$R_7$ is H, halogen, or a $C_1$–$C_6$alkyl, $C_1$–$C_6$alkoxy, aryl or heteroaryl group each optionally substituted;
$R_8$ is an optionally substituted $C_1$–$C_6$alkyl, aryl or heteroaryl group;
$R_{10}$, $R_{11}$, $R_{29}$ and $R_{30}$ are each independently H or an optionally substituted $C_1$–$C_6$alkyl group;
$R_{12}$, $R_{13}$ and $R_{17}$ are each independently H or an optionally substituted $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group;
$R_{14}$, $R_{15}$, $R_{16}$, $R_{18}$, $R_{19}$, $R_{26}$, $R_{27}$ and $R_{28}$ are each independently H or $C_1$–$C_4$alkyl;
$R_{20}$, $R_{22}$ and $R_{23}$ are each independently H or an optionally substituted $C_1$–$C_6$alkyl group;
$R_{24}$ and $R_{25}$ are each independently H or an alkyl, aryl or heteroaryl group each optionally substituted; and
--- represents a single bond or a double bond; or a pharmaceutically acceptable salt thereof.

10. The method according to claim 9 wherein said disorder is a mood disorder, a cognitive disorder or a motor disorder.

11. The method according to claim 10 wherein said disorder is anxiety or depression.

12. The method according to claim 9 wherein said disorder is schizophrenia.

13. The method according to claim 10 wherein said disorder is attention deficit disorder or memory loss.

14. The method according to claim 9 wherein said disorder is caused by alcohol or drug withdrawl.

15. A pharmaceutical composition which comprises a pharmaceutically acceptable carrier and an effective amount of a compound of formula I

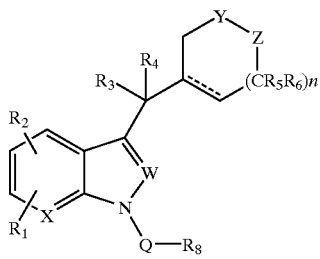

(I)

wherein
Q is $SO_2$, CO, $CONR_{24}$, $CSNR_{25}$;
W is N or $CR_7$;
X is N or $CR_9$;
Y is NR or $CR_{10}R_{29}$;
Z is $NR_{21}$ or $CR_{11}R_{30}$ with the proviso that when Y is NR then Z must be $CR_{11}R_{30}$ and with the further proviso that at least one of Y and Z must be NR or $NR_{21}$;
n is an integer of 1 or 2;
R and $R_{21}$ are each independently H, $CNR_{26}NR_{27}R_{28}$, or a $C_1$–$C_6$alkyl, $C_3$–$C_6$cycloalkyl, cycloheteroalkyl, aryl or heteroaryl group each optionally substituted;
$R_1$, $R_2$ and $R_9$ are each independently H, halogen, CN, $OCO_2R_{12}$, $CO_2R_{13}$, $CONR_{22}R_{23}$, $CNR_{14}NR_{15}R_{16}$, $SO_mR_{17}$, $NR_{18}R_{19}$, $OR_{20}$, or a $C_1$–$C_6$alkyl, $C_2$–$C_6$alkenyl, $C_2$–$C_6$alkynyl, $C_3$–$C_6$-cycloalkyl, cycloheteroalkyl, $C_1$–$C_6$alkanoyl, aryl or heteroaryl group each optionally substituted;
m is 0 or an integer of 1 or 2;
$R_3$ and $R_4$ are each independently H, halogen, $C_1$–$C_4$alkyl or $C_1$–$C_4$haloalkyl or $R_3$ and $R_4$ may be taken together with the atom to which they are attached to form a carbonyl group;
$R_5$ and $R_6$ are each independently H or an optionally substituted $C_1$–$C_6$alkyl group;
$R_7$ is H, halogen, or a $C_1$–$C_6$alkyl, $C_1$–$C_6$alkoxy, aryl or heteroaryl group each optionally substituted;
$R_8$ is an optionally substituted $C_1$–$C_6$alkyl, aryl or heteroaryl group;
$R_{10}$, $R_{11}$, $R_{29}$ and $R_{30}$ are each independently H or an optionally substituted $C_1$–$C_6$alkyl group;
$R_{12}$, $R_{13}$ and $R_{17}$ are each independently H or an optionally substituted $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group;
$R_{14}$, $R_{15}$, $R_{16}$, $R_{18}$, $R_{19}$, $R_{26}$, $R_{27}$ and $R_{28}$ are each independently H or $C_1$–$C_4$alkyl;
$R_{20}$, $R_{22}$ and $R_{23}$ are each independently H or an optionally substituted $C_1$–$C_6$alkyl group;
$R_{24}$ and $R_{25}$ are each independently H or an alkyl, aryl or heteroaryl group each optionally substituted; and
--- represents a single bond or a double bond; or a pharmaceutically acceptable salt thereof.

16. The composition according to claim 15 having a formula I compound wherein n is 1; and Q is $SO_2$ or CO.

17. The composition according to claim 16 having a formula I compound wherein $R_3$ and $R_4$ are H; and Q is $SO_2$.

18. The composition according to claim 17 having a formula I compound wherein X is $CR_9$; Y is $CR_{10}R_{29}$; Z is NH; $R_8$ is an optionally substituted aryl group; and = represents a single bond.

19. The composition according to claim 17 having a formula I compound selected from the group consisting of:

5-fluoro-1-(phenylsulfonyl)-3-(piperidin-4-ylmethyl)-1H-indole;
5-fluoro-1-(phenylsulfonyl)-3-(1,2,5,6-tetrahydro-3-pyridinylmethyl)-1H-indole;
4-{[5-fluoro-3-(4-piperidinylmethyl)-1H-indol-1yl]sulfonyl}aniline;
1-[(2,6-dichlorophenyl)sulfonyl]-5-fluoro-3-(4-piperidinylmethyl)-1H-indole;
1-[(3,4-dichloro-2-thienyl)sulfonyl]-5-fluoro-3-(4-piperidinylmethyl)-1H-indole;
5-fluoro-1-(1-naphthylsulfonyl)-3-(4-piperidinylmethyl)-1H-indole;
1-[(3,4-dimethoxyphenyl)sulfonyl]-5-fluoro-3-(piperidin-4-ylmethyl)-1H-indole;
4-{[5-fluoro-3-(piperidin-4-ylmethyl)-1H-indol-1-yl]sulfonyl}benzonitrile;
8-{[5-fluoro-3-(piperidin-4-ylmethyl)-1H-indol-1-yl]sulfonyl}quinoline;
1-(phenylsulfonyl)-3-(piperidin-4-ylmethyl)-1H-indole;
1-(1-naphthylsulfonyl)-3-(piperidin-4-ylmethyl)-1H-indole;
4-{[3-(piperidin-4-ylmethyl)-1H-indol-1-yl]sulfonyl}phenylamine;
1-[(3,4-dichlorothien-2-yl)sulfonyl]-3-(piperidin-4-ylmethyl)-1H-indole;
6-flouro-1-(phenylsulfonyl)-3-(4-piperidinylmethyl)-1H-indole;
6-flouro-1-(1-naphthylsulfonyl)-3-(4-piperidinylmethyl)-1H-indole;
6-flouro-1-(3,4-dimethoxyphenylsulfonyl)-3-(4-piperidinylmethyl)-1H-indole;
6-flouro-1-(2-chlorophenylsulfonyl)-3-(4-piperidinylmethyl)-1H-indole;
6-flouro-1-(5-chlorothien-2-ylsulfonyl)-3-(4-piperidinylmethyl)-1H-indole;
6-flouro-1-(2-fluorophenylsulfonyl)-3-(4-piperidinylmethyl)-1H-indole;
6-flouro-1-(3-fluorophenylsulfonyl)-3-(4-piperidinylmethyl)-1H-indole; and
a pharmaceutically acceptable salt thereof.

20. A process for the preparation of a compound of formula Ia'

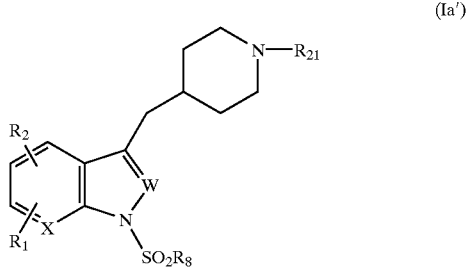

(Ia')

wherein
W is N or $CR_7$;
X is N or $CR_9$;
$R_1$, $R_2$ and $R_9$ are each independently H, halogen, CN, $OC_2R_{12}$, $CO_2R_{13}$, $CONR_{22}R_{23}$, $CNR_{14}NR_{15}R_{16}$, $SO_mR_{17}$, $NR_{18}R_{19}$, $Or_{20}$, or a $C_1$–$C_6$alkyl, $C_2$–$C_6$alkenyl, $C_2$–$C_6$alkynyl, $C_3$–$C_6$cycloalkyl, cycloheteroalkyl, $C_1$–$C_6$alkanoyl, aryl or heteroaryl group each optionally substituted;

m is 0 or an integer of 1 or 2;

$R_7$ is H, halogen, or a $C_1$–$C_6$alkyl, $C_1$–$C_6$alkoxy, aryl or heteroaryl group each optionally substituted;

$R_8$ is an optionally substituted $C_1$–$C_6$alkyl, aryl or heteroaryl group;

$R_{12}$, $R_{13}$ and $R_{17}$ are each independently H or an optionally substituted $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group;

$R_{14}$, $R_{15}$, $R_{16}$, $R_{18}$, $R_{19}$, $R_{26}$, $R_{27}$ and $R_{28}$ are each independently H or $C_1$–$C_4$ alkyl; and $R_{21}$ is H, $CNR_{26}NR_{27}R_{28}$, or a $C_1$–$C_6$alkyl, $C_3$–$C_6$cycloalkyl, cycloheteroalkyl, aryl or heteroaryl group each optionally substituted which process comprises reacting a compound of formula IVa wherein G represents a protecting group and W, X, $R_1$ and $R_2$ are as defined hereinabove with

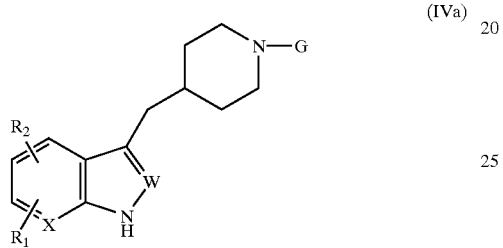
(IVa)

an arylsulfonyl chloride $R_8SO_2Cl$, wherein $R_8$ is as defined hereinabove in the presence of a base to form the intermediate of formula Va;

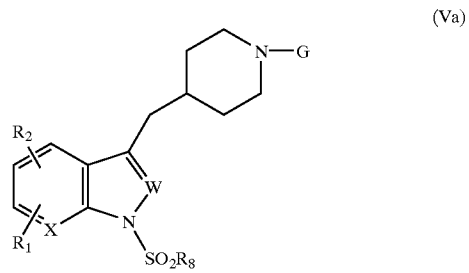
(Va)

deprotecting the formula Va compound in the presence of an acid to give the compound of formula Ia' wherein $R_{21}$ is H; and optionally reacting said formula Va compound with an alkylating agent, $R_{21}$-Hal, wherein Hal is Cl, I or Br and $R_{21}$ is other than H.

\* \* \* \* \*